United States Patent
Richmond

[11] Patent Number: 5,848,994
[45] Date of Patent: *Dec. 15, 1998

[54] IV SETS WITH NEEDLELESS SPIKELESS FITTINGS AND VALVES

[76] Inventor: Frank M. Richmond, 205 A Grant St., Harvard, Ill. 60033

[*] Notice: This patent issued on a continued prosecution application filed under 37 CFR 1.53(d), and is subject to the twenty year patent term provisions of 35 U.S.C. 154(a)(2).

[21] Appl. No.: 768,636

[22] Filed: Dec. 18, 1996

Related U.S. Application Data

[63] Continuation-in-part of Ser. No. 612,875, Mar. 12, 1996, Pat. No. 5,645,538, which is a continuation of Ser. No. 123,632, Sep. 16, 1993, Pat. No. 5,405,333, and a continuation-in-part of Ser. No. 377,514, Jan. 24, 1995, abandoned, which is a division of Ser. No. 98,499, Jul. 28, 1993, Pat. No. 5,445,623.

[51] Int. Cl.$^6$ .................................................... A61M 5/00
[52] U.S. Cl. ........................... 604/248; 604/246; 604/33; 604/30
[58] Field of Search ................................. 604/30, 33, 34, 604/9, 246, 247, 249, 256

[56] References Cited

U.S. PATENT DOCUMENTS

| | | |
|---|---|---|
| 2,387,955 | 10/1945 | Tilson . |
| 2,852,024 | 9/1958 | Ryan . |
| 4,059,109 | 11/1977 | Tischlinger . |
| 4,246,932 | 1/1981 | Raines . |
| 4,324,239 | 4/1982 | Gordon et al. . |
| 4,354,492 | 10/1982 | McPhee . |
| 4,468,225 | 8/1984 | Tchéraz ..................... 604/248 |
| 4,556,086 | 12/1985 | Raines . |
| 4,614,437 | 9/1986 | Buehler . |
| 4,623,343 | 11/1986 | Thompson ............... 604/405 |
| 4,683,916 | 8/1987 | Raines . |
| 4,838,875 | 6/1989 | Somor ...................... 604/262 |
| 4,852,560 | 8/1989 | Hermann, Jr. et al. . |
| 4,871,353 | 10/1989 | Thomsen .................... 604/80 |
| 4,898,581 | 2/1990 | Iwatschenko ............ 604/247 |
| 4,908,018 | 3/1990 | Thomsen .................. 604/247 |
| 4,915,687 | 4/1990 | Sivert ......................... 604/83 |
| 4,946,448 | 8/1990 | Richmond . |
| 4,998,926 | 3/1991 | Alchas ...................... 604/251 |
| 5,116,021 | 5/1992 | Faust et al. . |
| 5,163,922 | 11/1992 | McElveen, Jr. et al. ............... 604/249 |
| 5,190,067 | 3/1993 | Paradis et al. . |
| 5,232,111 | 8/1993 | Burns . |
| 5,391,150 | 2/1995 | Richmond ................. 604/111 |
| 5,405,333 | 4/1995 | Richmond ................. 604/257 |
| 5,445,623 | 8/1995 | Richmond ................. 604/251 |

*Primary Examiner*—Wynn Wood Coggins
*Assistant Examiner*—Jennifer R. Sadula
*Attorney, Agent, or Firm*—John L. Rogitz

[57] ABSTRACT

An IV set includes a drip chamber having a top end and a bottom end. A spikeless connector covers the top end, and an IV tube is connected to the bottom end of the drip chamber. The end of the IV tube opposite the drip chamber is engaged with a needleless/spikeless connector. Thereby, a needleless/spikeless IV set is rendered. A reflux valve including a deformable valve member and reciprocating valve element is also disclosed for use in conjunction with the needleless/spikeless IV connectors.

25 Claims, 6 Drawing Sheets

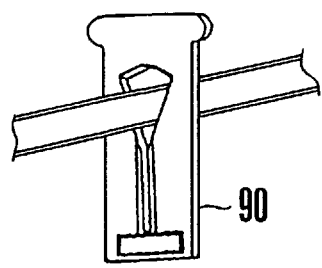
Fig. 8A
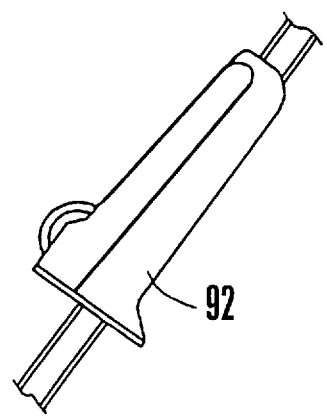
Fig. 8B
Fig. 8C
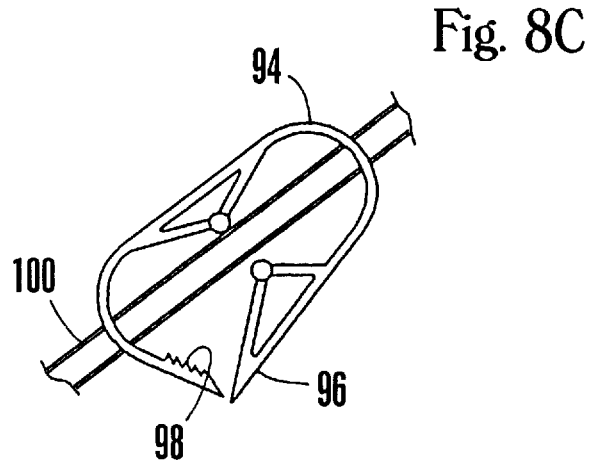

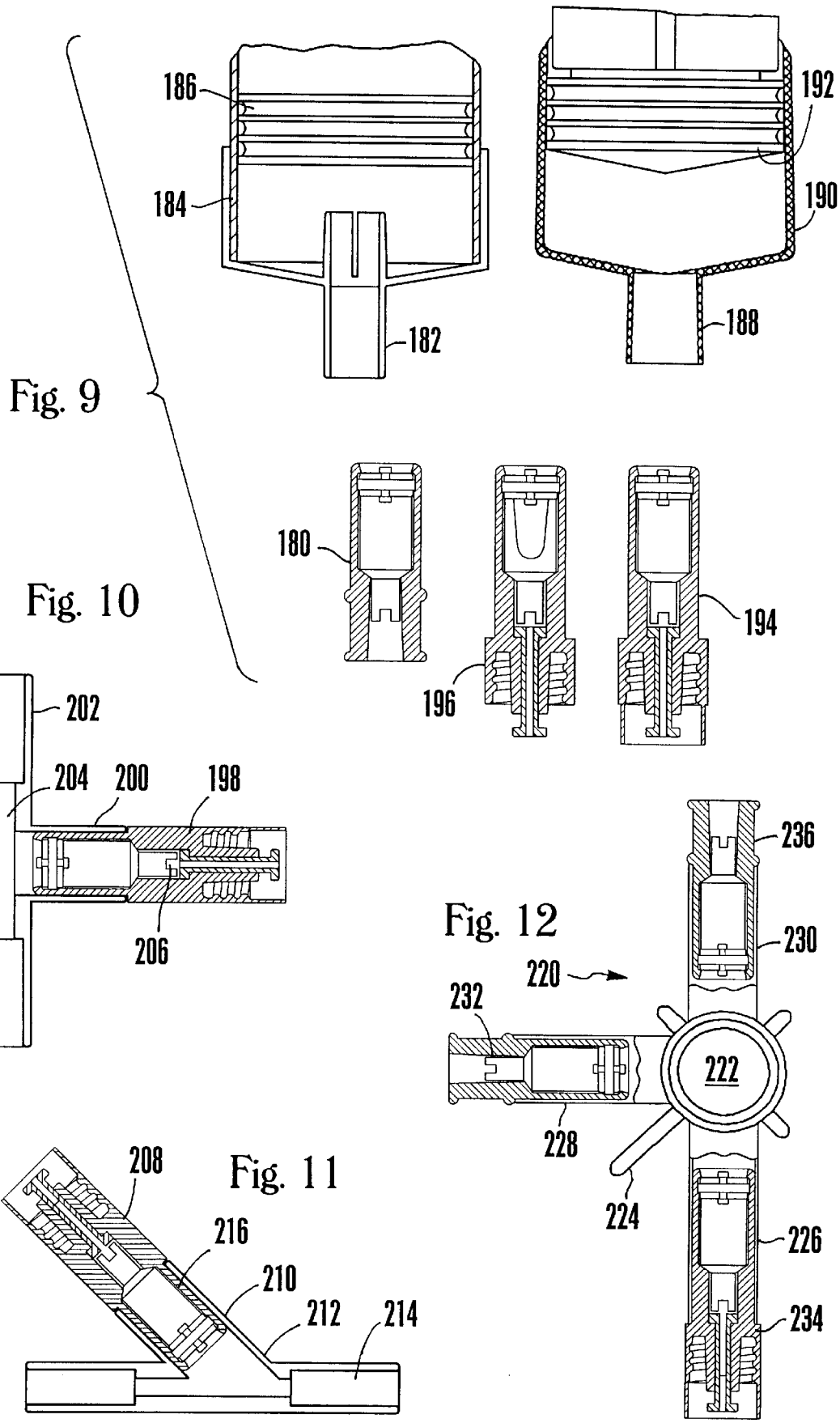

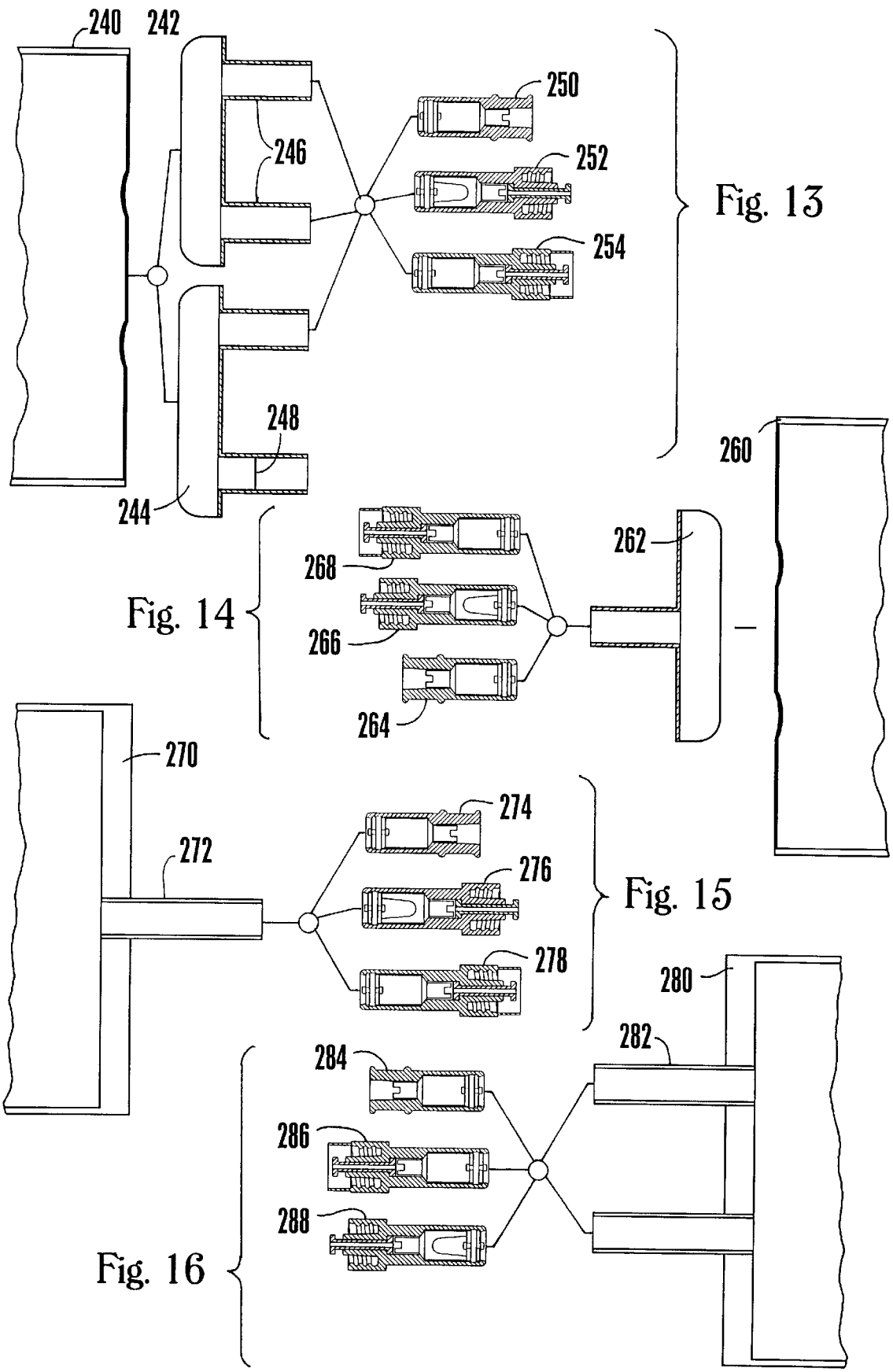

IV SETS WITH NEEDLELESS SPIKELESS FITTINGS AND VALVES

RELATED APPLICATIONS

This is a continuation in part of U.S. patent application Ser. No. 08/612,875, filed Mar. 12, 1996, now U.S. Pat. No. 5,645,538, which in turn is a continuation of U.S. patent application Ser. No. 08/123,632, filed Sep. 16, 1993, now U.S. Pat. No. 5,405,333; This is also a continuation in part of U.S. patent application Ser. No. 08/377,514, filed on Jan. 24, 1995, now abandoned, which is a divisional of U.S. patent application Ser. No. 08/098,499, filed Jul. 28, 1993, now U.S. Pat. No. 5,445,623.

FIELD OF THE INVENTION

The present invention relates generally to intravenous (IV) liquid medicament infusion equipment, and more particularly to needleless IV sets.

BACKGROUND OF THE INVENTION

One of the most widely used methods of medical therapy is the intravenous (IV) infusion of liquid medicaments and/or nutrients into the bloodstream of a patient. A familiar apparatus that is used in many IV infusion applications is an IV container, such as an IV bag or bottle, which contains the liquid to be infused into the patient.

When the IV container is a bag, a rigid, hollow, sharpened IV spike is pushed into the bag to establish a pathway for fluid communication through which the liquid can flow out of the bag. The spike, in turn, is connected to or formed integrally with an inlet port of a small, elongated, transparent hollow container familiarly referred to as a "drip chamber", with the fluid pathway of the spike in fluid communication with the inlet port of the drip chamber.

Additionally, an IV line is connected to an outlet port (which usually is located below the inlet port) of the drip chamber. Preferably, a flow control clamp (such as a roller clamp or other suitable flow regulating device) is engaged with the IV line, and a medical technician can manipulate the flow control clamp to squeeze the IV line and thereby regulate fluid flow through the IV line. To establish a path for fluid communication from the IV container to the patient, a sharp needle is connected to the IV line to puncture the patient. Together, the drip chamber with outlet tube and clamp is referred to as an "IV set".

Usually, the bag or bottle is elevated above the patient to establish a positive pressure head to force the fluid that is within the bag or bottle through the drip chamber into the patient. Because the drip chamber is transparent, a medical technician can view the medicament as it passes (normally by dripping) through the drip chamber to aid the medical technician in establishing a predetermined flow rate of medicament into the patient as the medical technician adjusts the roller clamp on the IV line. This set can also be used with a pump or fluid delivery system.

While effective as aids in establishing a predetermined fluid flow through the patient, existing IV sets, as noted above, require the use of sharpened spikes to puncture the IV container containing the liquid. This is undesirable, particularly in the era of AIDS, because "sharps" can and do inadvertently puncture medical technicians who manipulating them, thereby potentially infecting the technician with AIDS or other disease. Thus, as recognized by the present invention, it is desirable to avoid the use of sharp instruments whenever possible.

Further, it is desirable to connect and disconnect components of IV sets easily, conveniently, and without spillage of medicament. As recognized by the present invention, such reduction in spillage can be obtained through the use of reflux valves which are compatible with needleless drip chambers and other needleless IV components.

Accordingly, it is an object of the present invention to provide an IV set which does not require the use of "sharps". Another object of the present invention is to provide an IV set which is easy to use and cost-effective to manufacture. A further object of the present invention is to provide a valve apparatus in an IV component for engaging a complementary fitting, without the need to use a sharp connector.

SUMMARY OF THE INVENTION

An IV set includes an elongated drip chamber having a top end and a bottom end. The drip chamber is transparent for viewing liquid dripping from the top end toward the bottom end. An upper needleless connector is engaged with the top end of the drip chamber for connecting the top end to a needleless fitting, and an IV line is connected to the bottom end of the drip chamber. A lower needleless connector is engaged with the IV line to connect the IV line to a needleless fitting.

In a preferred embodiment, at least one of the needleless connectors is a valve including a valve body configured as a Luer fitting. The valve also includes a resilient valve member disposed in the valve body and defining an outer periphery that is uninterrupted within the periphery. The valve member is biased to a first configuration, wherein a passageway for fluid communication is not established through the connector. In accordance with the present invention, the member is deformable to a second configuration, wherein fluid communication through the opening is permitted. As disclosed in detail below, the valve can include a male valve element disposed in the valve body. This valve element defines an engagement surface that extends outwardly beyond the valve body for contacting a spikeless/needleless connector to cause the valve element to move against the valve member and deform the valve member to the second configuration.

If desired, a protective collar can be connected to the valve body and extend away therefrom. In one embodiment, the collar is a tamper-evident collar having ratchet teeth. In another embodiment, the valve member is formed with a skirt defining a surface having an opening formed therein. Also, a flow constrictor can be engaged with the IV line for regulating fluid flow therethrough.

In another aspect, a valve includes a valve body configured as a Luer fitting and a resilient valve member disposed in the valve body and biased to a first configuration, wherein a passageway for fluid communication is not established through the valve body. Per the present invention, the member is deformable to a second configuration, wherein fluid communication through the valve body is permitted. A male valve element is disposed in the valve body, and the valve element defines an engagement surface that extends outwardly beyond the valve body for contacting a spikeless/needleless connector to cause the valve element to move against the valve member and deform the valve member to the second configuration.

In still another aspect, a method for engaging a drip chamber with an IV container and an IV component to which it is desired to establish fluid flow from the IV container includes engaging an upper needleless connector to a top end of the drip chamber. The method also includes engaging the upper needleless connector with a needleless connector in fluid communication with the IV container, such that fluid can flow from the IV container to the top end of the drip chamber. An IV tube is connected to a bottom end of the drip chamber, with the IV tube defining an end opposed to the drip chamber relative to the tube. The present method further includes engaging a lower needleless connector to the end of the IV line, and engaging the lower needleless connector with a needleless connector in fluid communication with the IV component, such that fluid can flow from the IV container, through the drip chamber, and to the IV component.

These and other aspects of the present invention can best be appreciated in reference to the accompanying drawings in which like numerals refer to like parts, and in which:

BRIEF DESCRIPTION OF THE DRAWINGS

FIG. 8A is a perspective view of an alternate IV line flow restrictor;

FIG. 8B is a side view of another alternate IV line flow restrictor;

FIG. 8C is a side view of still another alternate IV line flow restrictor;

FIG. 9 is an exploded cross-sectional view showing male and female reflux valves in combination with two types of syringes;

FIG. 10 is a cross-sectional view of a male reflux valve bonded to a "T"-site connector;

FIG. 11 is a cross-sectional view of a male reflux valve bonded to a "Y"-site connector;

FIG. 12 is a plan cross-sectional view of a plurality of reflux valves operably engaged with a stopcock;

FIG. 13 is an exploded cross-sectional view of a liquid medicament bag having various reflux valves in combination with saddle ports, with portions of the bag broken away;

FIG. 14 is an exploded cross-sectional view of a liquid medicament bag having various reflux valves in combination with a single saddle port, with portions of the bag broken away;

FIG. 15 is an exploded cross-sectional view of a liquid medicament bag having various reflux valves in combination with a conventional port, with portions of the bag broken away;

FIG. 16 is an exploded cross-sectional view of a liquid medicament bag having various reflux valves in combination with two conventional ports, with portions of the bag broken away;

DESCRIPTION OF THE PREFERRED EMBODIMENT

Figure 1:
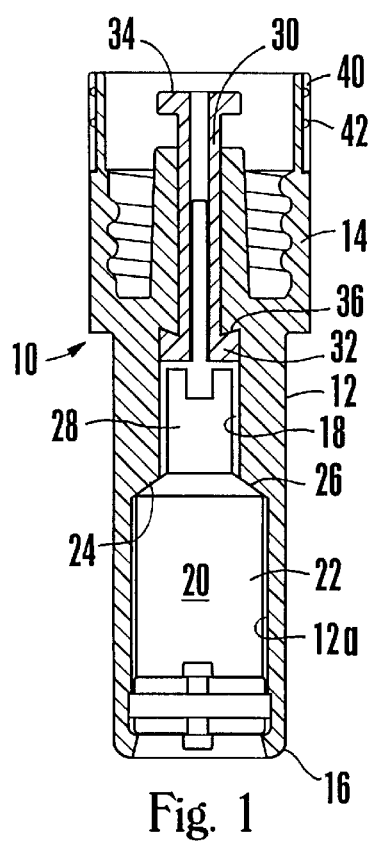
FIG. 1 is a partial cross-sectional view of a male reflux valve of the present invention shown disposed in a male Luer fitting, with a tamper evident collar.

Referring initially to FIG. 1, an intravenous (IV) male reflux valve is shown and generally designated 10. As shown, the valve 10 includes a hollow plastic molded valve body 12 having a first end 14 configured like a male Luer fitting and a second end 16. A fluid passageway 18 is established through the valve body 12, from end 14 to end 16. As those skilled in the art will recognize, male Luer fittings need not have the threaded cylindrical outer flange shown in FIG. 1.

To selectively block the fluid passageway 18, a valve member 20 is disposed therein. As shown, the valve body 12 is formed with a plurality of longitudinal wall ribs 12a for contacting a hollow deformable resilient cylindrical skirt 22 defining a frusto-conical shoulder 24. Also, the valve body 12 is formed with a frusto-conical seat 26, and as shown in FIG. 1 the valve member 20 is materially biased to a closed configuration, wherein the shoulder 24 flushly contacts the seat 26 to thereby block the fluid passageway 18. Moreover, pressure can be exerted against a stem 28 of the valve member 20 to deform the valve member 20 to an open configuration, such that the shoulder 24 is distanced from the seat 26. In the open configuration, fluid can pass between the shoulder 24 and seat 26, and the fluid passageway 18 consequently is unblocked.

Figure 2:
FIG. 2 is a cross-sectional detail view of the valve shown in FIG. 1, showing the valve element-valve member interface.

FIG. 1 additionally shows that a hollow elongated rigid plastic valve element 30 is reciprocably disposed in the fluid passageway 18. The valve element 30 is formed with a lower contact flange 32 and an upper contact flange 34. As shown, the lower contact flange 32 retains the valve element 30 in the valve body 12 by contacting a flange surface 36. Referring briefly to FIG. 2, both the flange surface 36 and lower contact flange 32 define an obtuse angle with respect to the long axis 38 of the fluid passageway 18, to thereby promote the retention of the valve element 30 within the valve body 12.

Referring back to FIG. 1, it can now be understood that the male Luer fitting-configured end 14 of the valve 10 can be engaged with a complementarily-shaped female Luer fitting (not shown), and that by so engaging the valve 10, the upper contact flange 34 of the valve element 30 is contacted by the female Luer fitting to urge the valve element 30 downwardly. When the valve element 30 is urged sufficiently downwardly, it in turn contacts the valve member 20 and urges the valve member 20 to the open configuration, to thereby unblock the fluid passageway 18.

Figure 3:
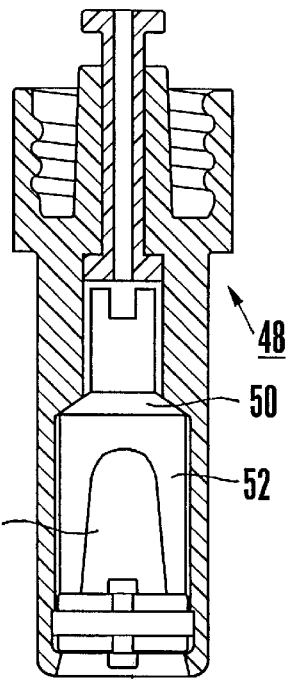
FIG. 3 is a cross-sectional view of a male reflux valve of the present invention shown disposed in a male Luer fitting, with a protection collar.
Figure 4:
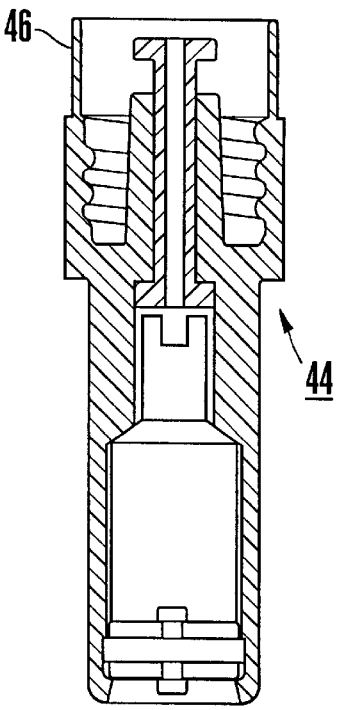
FIG. 4 is a cross-sectional view of a male reflux valve of the present invention shown disposed in a male Luer fitting, with no collar.

If desired, a cylindrical tamper evident collar 40 can be formed integrally with and extend away from the first end 14 of the valve 10, with the male valve element 30 protruding beyond the first end 14 but not beyond the end of the collar 40. The tamper evident collar 40 includes teeth 42 that ratchetably engage a tamper cap (not shown) in accordance with principles well-known in the art. Alternatively, as shown in FIG. 3 a male reflux valve 44 can be formed with a smooth protective collar 46. Or, as shown in FIG. 4, a male reflux valve 48 can be formed without a collar, and a valve member 50 can have a skirt 52 that need not define a continuous cylindrical surface, but rather can be formed with an opening 54. Hereinafter, the male reflux valves shown in FIGS. 1–4 are referred to as male member valves.

Figure 5:
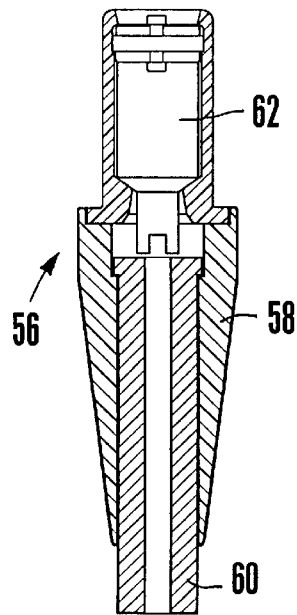
FIG. 5 is a cross-sectional view of a male reflux valve in operable engagement with a tapered adapter fitting.
Figure 6:
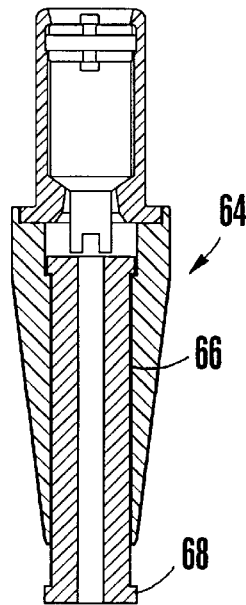
FIG. 6 is a cross-sectional view of a flanged male reflux valve in operable engagement with a tapered adapter fitting.
Figure 7:
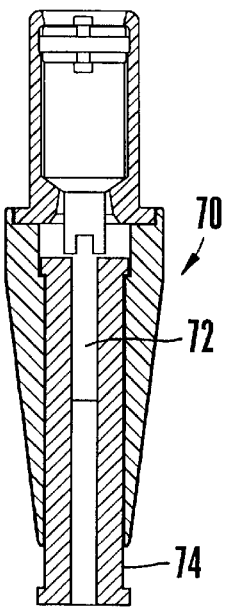
FIG. 7 is a cross-sectional view of another flanged male reflux valve in operable engagement with a tapered adapter fitting.

FIGS. 5–7 show that the valve body need not be formed as a Luer fitting, but can alternatively be formed as a Foley catheter adaptor. Specifically, FIG. 5 shows a male reflux valve 56 that has a tapered body 58, with an elongated valve element 60 reciprocably disposed therein for urging a valve member 62 to an open configuration. The valve element 60 does not have a Luer fitting contact flange. The valve 56 shown in FIG. 5 is in all other substantial respects identical in configuration and operation to the valve 10 shown in FIG. 1. FIG. 6 shows that a valve 64 can have a valve element 66 formed with a Luer fitting contact flange 68. The valve 64 shown in FIG. 6 is in all other substantial respects identical in configuration and operation to the valve 56 shown in FIG. 5. Also, FIG. 7 shows a valve 70 that has a central guide 72 extending into a valve element 74.

Figure 8:
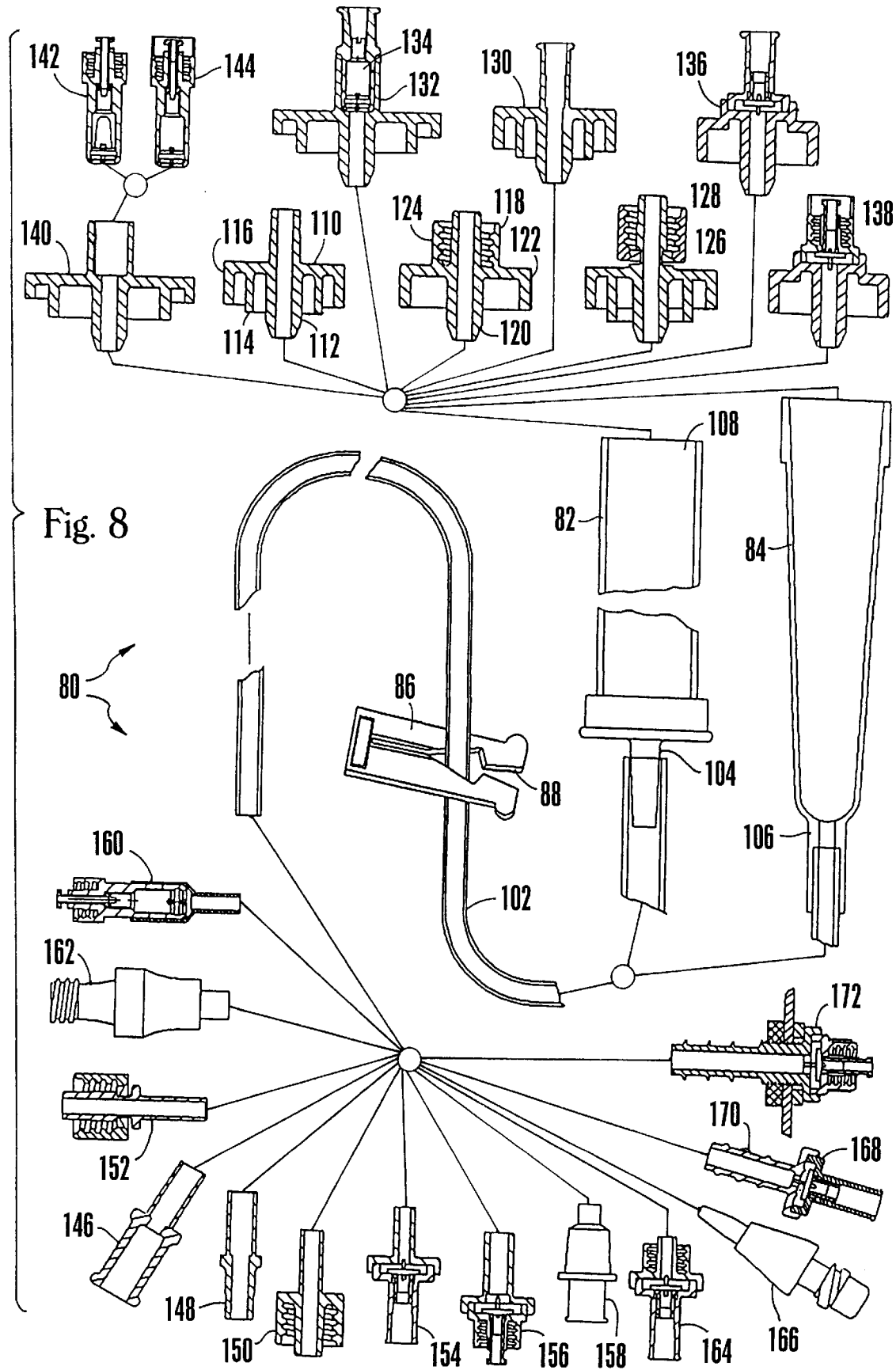
FIG. 8 is a partial cross-sectional view of an IV set of the present invention, showing various drip chamber upper connections and various drip chamber lower connections in exploded relationships.

Now referring to FIG. 8, an IV set is shown, generally designated 80. As can be appreciated in reference to FIG. 8, the present IV set includes a drip chamber, an upper needleless connector on the top of the drip chamber to connect the top to a needleless fitting (such as any of those shown herein), an IV tube connected to the bottom of the drip chamber, a flow restrictor engaged with the IV tube, and a lower needleless connector connected to the end of the IV tube to connect the tube to a needleless fitting (such as any of those shown herein).

As shown in FIG. 8, the drip chamber can be an elongated hollow transparent plastic cylindrical drip chamber 82 or tapered drip chamber 84. In any case, the present drip chamber is "elongated" in that its length is at least half again as great as its diameter. The IV tube is a hollow plastic IV tube known in the art, with the flow restrictor being an open slide clamp 86 having an open head end 88 (FIG. 8), a closed slide clamp 90 (FIG. 8A), a roller clamp 92 (FIG. 8B), or a ratchet clamp 94 having a resilient arm 96 that can be ratchetably engaged with a pawl 98 to restrict flow through an IV tube 100. The ratchet clamp 94 is made by Halkey-Roberts (FIG. 8C), and the operation of all of the above-described clamps is known in the art.

In the particular embodiment shown in FIG. 8, an IV tube 102 can be connected by attaching the tube 102 by means well-known in the art to an exit port 104 of the cylindrical drip chamber 82 or to and exit port 106 of the tapered drip chamber 84. For succinctness of disclosure, the discussion below will focus on the cylindrical drip chamber 82, but it is to be understood that the discussion below is equally relevant to the tapered drip chamber 84 or indeed any well-known drip chamber. The open clamp 86 can be manipulated by means well-known in the art to constrict the IV tube 102 to stop fluid flow therethrough.

As shown in FIG. 8, the drip chamber 82 has an upper opening 108 that is engaged with one of the upper needleless connectors shown (each of which has a drip-forming tube) by means well-known in the art (e.g., adhesive bonding, ultra-sonic welding, solvent bonding, heat staking, spin welding or rf sealing). As used herein, the term "needleless" encompasses spikeless, needleless, and other the other non-sharp connectors shown. Alternatively, the upper connector can be formed integrally with the drip chamber 82. In accordance with the present invention, the upper needleless connector is engaged with a complementarily-configured connector of an IV bag or IV pump.

In the preferred embodiments shown, the upper needleless connector can be any one of a collarless male Luer fitting 110 having a central drip forming tube 112, an inner ring 114, and an outer ring 116, with the wall of the drip chamber 82 being held between the inner and outer rings 114, 116. Or, the upper needleless connector can be a male Luer fitting 118 having a central drip-forming tube 120 and a single ring 122 that grips the exterior of the drip chamber 82. As shown, the male Luer fitting 118 includes a stationary collar 124. Alternatively, a male Luer fitting 126 having a rotatable collar 128 can serve as the upper needleless connector.

Still further, the upper needleless connector can be a female Luer fitting 130. Yet again, the upper needleless connector can be a valve 132 that is configured as a female Luer fitting as shown and that includes a valve member 134 that is in all essential respects identical to the valve member 20 shown in FIG. 1. Hereinafter, the valve 132 is referred to as a female member valve.

Moreover, the upper needleless connector can be a female disc valve 136. Details of the female disc valve are disclosed in the third of the above-referenced patents. Still further, the upper needleless connector can be a male member valve 138 that is in all essential respects identical to the valve 10 shown in FIG. 1. Or, the upper needleless connector can be include a drip chamber adaptor fitting 140 in combination with one of a male member valve 142 or 144 as shown.

FIG. 8 further shows that a lower needleless connector is provided on the end of the IV tube 102 that is distanced from the drip chamber 82. As indicated in FIG. 8, the lower needleless connector can be any one of a female Luer fitting 146, a collarless male Luer fitting 148, a male Luer fitting 150 having a stationary collar, and a male Luer fitting 152 having a rotatable collar. Additionally, the lower needleless connector can be a female disc valve 154 or a male disc valve 156, the details of which are disclosed in the third of the above-referenced U.S. patents. Further, the lower needleless connector can be a female member valve 158 or male member valve 160. Also, the lower needleless connector can be a reflux valve 162 made by Clave, or a so-called "safe site" female reflux valve 164 made by Burron. Further, the lower needleless connector can be a connector 166 made by Baxter and referred to as an "interlink style connection". And, the lower needleless connector can be a female disc valve 168 having a barbed shaft 170 that is insertable into the IV tube 102, or a male disc valve 172 having a bulkhead fitting configuration as shown. The bulkhead fitting can advantageously be similar to any one of the Luer bulkhead fittings made by Value Plastics, Inc. of Fort Collins, Colo.

With the above disclosure in mind, it can be appreciated that the present IV set includes a conventional drip chamber which can be connected to other components at both its top end and bottom end using the novel needleless connectors of the present invention. Thereby, the risk of punctures to medical personnel is reduced, and the ease of use of the IV set of the present invention is greater than that of conventional IV sets.

In addition to the IV set shown and described above, the female and male member valves of the present invention can be used in conjunction with other IV components. For example, FIG. 9 shows that a female member valve 180 can be used to selectively block the discharge port 182 of a syringe 184 having a flat-end plunger 186 that contains a frangible barrier within the plunger. An example of this type of plunger is made by Smith & Nephew. The female member valve 180 can also be used to block the discharge port 188 of a syringe 190 having a frusto-conical end plunger 192. As recognized by the present invention, with this structure the syringe 190 can be used as a pre-filled syringe. Alternatively to the female member valve, a male member valve 194, which is essentially identical to valve 10 shown in FIG. 1, or a male member valve 196, which is essentially identical to the valve 48 shown in FIG. 4, can be used in lieu of the female member valve 180. It is to be understood that this configuration can be used with multi-chamber syringes that are disclosed in U.S. Pat. Nos. 5,298,024 and 5,476,449.

FIG. 10 shows a male member valve 198 which is disposed in a port 200 of a so-called "T"-site connector 202. The T-site connector 202 defines a main fluid passageway 204 and a secondary fluid passageway 206, and the male member valve 198 can be manipulated as described above to selectively permit fluid communication through the secondary fluid passageway 206 of the T-site connector 202.

FIG. 11 shows a male member valve 208 which is disposed in a port 210 of a so-called "Y"-site connector 212. As shown, the Y-site connector 212 defines a main cylindrical fluid passageway 214 and a secondary fluid passageway 216. The valve 208 can be operated as disclosed above to selectively block fluid communication through the secondary passageway 216 of the Y-site connector 212.

FIG. 12 shows an IV stopcock, generally designated 220. In accordance with principles well known in the art, the stopcock 220 includes a central fluid passageway that is covered by a cover plate 222, and an operating hand wheel 224. Additionally, the stopcock 220 can include at least two ports, and can include additional ports. In the embodiment shown in FIG. 12, the stopcock 220 includes first, second and third ports 226, 228, 230. A respective member valve is disposed in each one of the ports 226, 228, 230 to selectively establish fluid communication through the port. More particularly, a first female member valve 232 is disposed in the second port 228, a male member valve 234 is disposed in the first port 226, and a second female reflux valve 236 is disposed in the third port 230. It is to be understood that one or more of the ports 226, 228, 230 may not include a valve, and that for the embodiment shown in FIG. 12, i.e. a stopcock 220 having three ports, one of the ports will contain a male member valve while the remaining ports will contain male/female member valves.

FIG. 13 shows that the member valves of the present invention can be used in connection with an IV bag 240 that is made of a suitable inert, biocompatible, flexible material, such as polyvinylchloride (PVC) or plex dr. It is to be understood, however, that the principles of the present invention can be applied to other types of IV fluid containers, such as semi-rigid containers (not shown), multi-layer bags for holding cell culture, or glass bottles and vials.

As shown in FIG. 13, the bag 240 can be engaged by means well-known in the art with any one of a saddle port 242 or 244. In turn, each saddle port 242, 244 defines a plurality of ports 246. As shown, one of the ports 246 can be blocked by a conventional frangible membrane 248. The other three ports 246 can be selectively blocked by engaging the ports 246 with one of a female member valve 250, male member valve 252 that is essentially identical to the valve 48 shown in FIG. 4, or male member valve 254 that is essentially identical to the valve 10 shown in FIG. 1. The saddle ports can equivalently be so-called "wedge" ports, "boat" ports, and other equivalent ports, such as is disclosed in my issued U.S. Pat. No. 5,405,333, incorporated herein by reference.

FIG. 14 shows that an IV bag 260 can include a single-port saddle port 262, and the port of the saddle port 262 can be selectively blocked by any one of a female member valve 264, first male member valve 266, or second male member valve 268. Alternatively, the valve members of the present invention can be used to block so-called "belly button" ports on the sides of IV bags, as disclosed in my issued U.S. Pat. No. 5,405,333.

In contrast, FIG. 15 shows that an IV bag 270 having a single conventional tube port 272 can be associated with any one of a female member valve 274, first male member valve 276, or second male member valve 278 to selectively block the tube port 272. On the other hand, FIG. 16 shows that an IV bag 280 having two or more conventional tube ports 282 can be associated with one or more of a female member valve 284, first male member valve 286, or second male member valve 288 to selectively block one or both of the tube ports 282.

Figure 17:
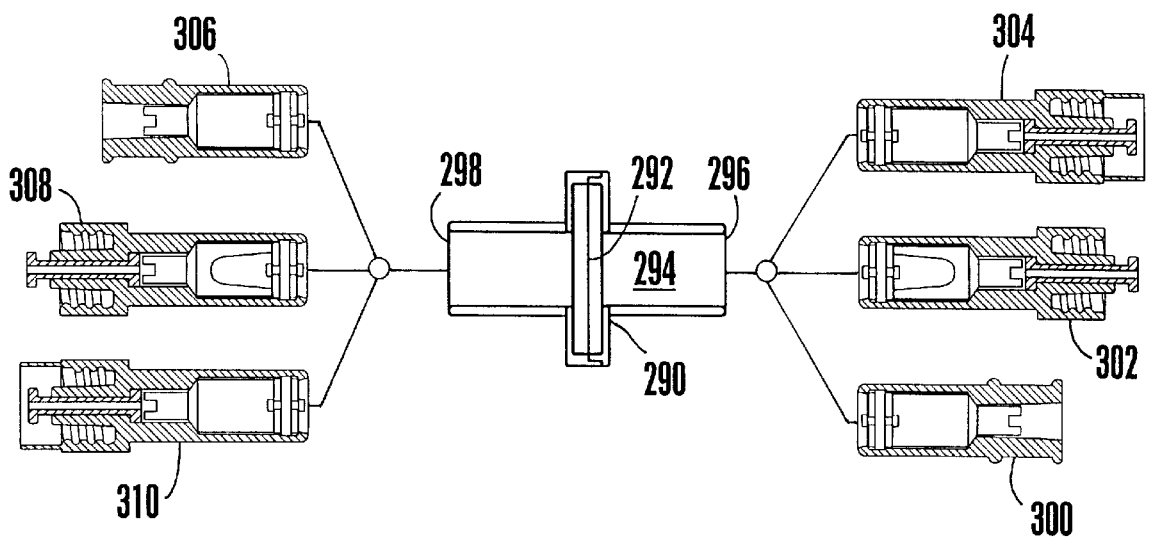
FIG. 17 is an exploded cross-sectional view of various reflux valves in combination with a filter assembly.
Figure 18:
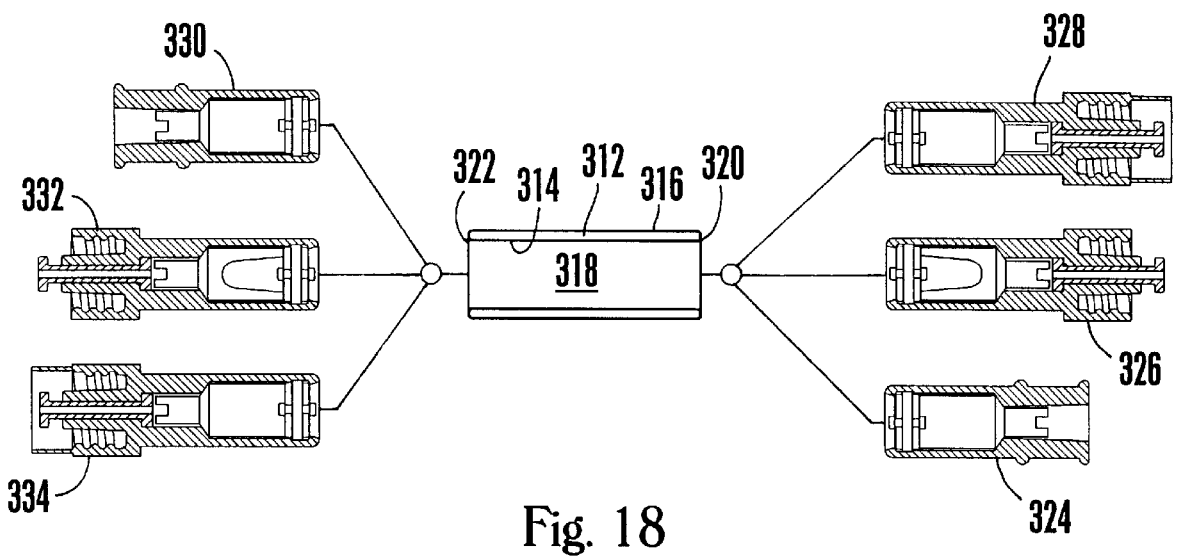
FIG. 18 is an exploded cross-sectional view of various reflux valves in combination with a tubular connectors.

FIGS. 17 and 18 show yet further applications for the male and female member valves of the present invention. It may now be understood that the valve of the present invention is joined to an intravenous (IV) component by means well known in the art, e.g., solvent bonding, RF sealing, heat staking, spin welding, or sonic welding, and that the IV component can be any IV component for which it is desired to selectively establish fluid communication into or out of.

For example, as shown in FIG. 17, the IV component can be a tubular IV connector 290 having a filter 292 disposed athwart a fluid passageway 294 defined by the connector 290. The connector 290 has an inlet port 296 and an outlet port 298. The inlet port 296 can be selectively blocked by engaging the port 296 with any one of a female member valve 300, a first male member valve 302, or a second male member valve 304. Similarly, the outlet port 298 can be selectively blocked by engaging the port 298 with any one of a female member valve 306, a first male member valve 308, or a second male member valve 310. Accordingly, the IV component shown in FIG. 17 is resealable, in that upon disconnecting a fitting from the valve member in one of the ports 296, 298, fluid flow through the component is prevented by the valve member in the disconnected port.

FIG. 18 shows a connector 312 having cylindrical inner and outer walls 314, 316. The connector 312 defines a fluid passageway 318 and first and second open ends 320, 322. The first open end 320 can be selectively blocked by engaging the end 320 with any one of a female member valve 324, a first male member valve 326, or a second male member valve 328. Similarly, the second open end 322 can be selectively blocked by engaging the end 322 with any one of a female member valve 330, a first male member valve 332, or a second male member valve 334.

While the particular needleless connector for use with intravenous infusion components as herein shown and described in detail is fully capable of attaining the objects stated above, it is to be understood that it is but the presently preferred embodiments of the present invention, and that the scope of the present invention is accordingly to be limited by nothing other than the appended claims.

I claim:

1. A valve, comprising:
   a valve body configured as a Luer fitting;
   a resilient valve member defining an outer periphery that is uninterrupted within the periphery disposed in the valve body and biased to a first configuration, wherein a passageway for fluid communication is not established through the valve body, the member being movable to a second configuration, wherein fluid communication through the valve body is permitted; and
   a male valve element disposed in the valve body and defining an engagement surface extending outwardly beyond the valve body for contacting a spikeless/needleless connector to cause the valve element to move against the valve member and move the valve member to the second configuration.

2. The valve of claim 1, further comprising a collar connected to the valve body and extending away therefrom.

3. The valve of claim 2, wherein the collar is a tamper-evident collar having ratchet teeth.

4. The valve of claim 1, wherein the valve member is formed with a skirt defining a surface having an opening formed therein.

5. The valve of claim 1, wherein the valve body is configured as a male Luer fitting having a collar.

6. The valve of claim 5, wherein the collar is rotatable relative to the valve member.

7. The valve of claim 1, in combination with a drip chamber.

8. The valve of claim 1, in combination with an IV container.

9. The valve of claim 1, in combination with a stopcock.

10. The valve of claim 1, in combination with a T-fitting.

11. The valve of claim 1, in combination with a Y-fitting.

12. The valve of claim 1, in combination with an adaptor.

13. The valve of claim 1, in combination with a syringe.

14. A syringe having a discharge port and a connector disposed in the discharge port to selectively block the discharge port, the connector being configured as a female Luer fitting having a resilient valve member in a body and biased to a first configuration, wherein a passageway for fluid communication is not established through the connector, the member being movable to a second configuration, wherein fluid communication is permitted.

15. An IV disposable system that reseals when disconnected, comprising:

a distal end configured as a Luer fitting with a resilient valve member defining an outer periphery that is uninterrupted within the periphery, disposed in the distal end and biased to a first a first configuration, wherein a passageway for fluid communication is not established through the system, the member being movable to a second configuration, wherein fluid communication is permitted;

an intermediate structure; and a proximal end configured as a Luer fitting with a resilient valve member defining an outer periphery that is uninterrupted within the periphery, disposed in the proximal end and biased to a first a first configuration, wherein a passageway for fluid communication is not established through the system, the member being movable to a second configuration, wherein fluid communication is permitted, the intermediate structure interconnecting the distal and proximal ends.

16. The IV disposable system of claim 15, wherein one of the distal and proximal ends is configured as a male Luer fitting and one of the proximal and distal ends is configured as a female Luer fitting.

17. The IV disposable system of claim 15, wherein both the proximal and distal ends are configured as a male Luer fitting.

18. The IV disposable system of claim 15, wherein both the proximal and distal ends are configured as a female Luer fitting.

19. The IV disposable system of claim 15, wherein the intermediate structure is an intravenous infusion set including at least an intravenous infusion line extending between the proximal and distal ends.

20. The IV disposable system of claim 15, wherein the structure is an adaptor.

21. The IV disposable system of claim 15, wherein the structure is a Y-site.

22. The IV disposable system of claim 15, wherein the structure is a T-site.

23. The IV disposable system of claim 15, wherein the structure is a drip chamber.

24. The IV disposable system of claim 15, wherein the structure is a stopcock with at least two ports.

25. The IV disposable system of claim 15, wherein the structure is a filter.

* * * * *

UNITED STATES PATENT AND TRADEMARK OFFICE
CERTIFICATE OF CORRECTION

PATENT NO. : 5,848,994
DATED : December 15, 1998
INVENTOR(S) : Richmond

It is certified that error appears in the above-indentified patent and that said Letters Patent is hereby corrected as shown below:

Claim 15, column 9, line 38, delete the second occurrence of "a first."

Claim 15, column 10, line 7, delete the second occurrence of "a first."

Claim 16, column 10, line 14, after "distal" change "and" to --or--.

Claim 16, column 10, line 15, after "proximal" change "and" to --or--.

Signed and Sealed this

Eighth Day of June, 1999

Q. TODD DICKINSON

*Attest:*

*Attesting Officer*  *Acting Commissioner of Patents and Trademarks*